(12) United States Patent
Franzi et al.

(10) Patent No.: US 12,285,269 B2
(45) Date of Patent: Apr. 29, 2025

(54) METHOD OF TRANSMISSION BY A WATCH OF AN INFORMATION MESSAGE RELATING TO AN ASSESSMENT OF THE SLEEP QUALITY OF A USER OF SAID WATCH

(71) Applicant: Tissot SA, Le Locle (CH)

(72) Inventors: Edoardo Franzi, Cheseaux-Noreaz (CH); Andrea Dunbar, St-Blaise (CH); Engin Turetken, Ecublens (CH); Virginie Moser, Diesse (CH); Patrick Stadelmann, Boudry (CH); Lingchuan Zhou, Marin-Epagnier (CH)

(73) Assignee: Tissot SA, Le Locle (CH)

( * ) Notice: Subject to any disclaimer, the term of this patent is extended or adjusted under 35 U.S.C. 154(b) by 127 days.

(21) Appl. No.: 16/596,911

(22) Filed: Oct. 9, 2019

(65) Prior Publication Data
US 2020/0129121 A1 Apr. 30, 2020

(30) Foreign Application Priority Data
Oct. 26, 2018 (EP) ..................................... 18202782

(51) Int. Cl.
*A61B 5/00* (2006.01)

(52) U.S. Cl.
CPC ............ *A61B 5/681* (2013.01); *A61B 5/4815* (2013.01); *A61B 5/4857* (2013.01); *A61B 5/72* (2013.01)

(58) Field of Classification Search
CPC ..... A61B 5/681; A61B 5/4815; A61B 5/4857; A61B 5/72; A61B 2560/0242;
(Continued)

(56) References Cited

U.S. PATENT DOCUMENTS 6,392,962 B1 * 5/2002 Wyatt ....................... G04F 8/08
368/110
9,820,680 B2 * 11/2017 Muzet ................ A61B 5/02405
(Continued)

FOREIGN PATENT DOCUMENTS

CN        103228203 A    7/2013
EP        1 163 878 A1    12/2001
(Continued)

OTHER PUBLICATIONS

Japanese Office Action issued Nov. 24, 2020 in Japanese Patent Application No. 2019-192558 (with English translation). 5 pages.
(Continued)

*Primary Examiner* — Tammie K Marlen
*Assistant Examiner* — Ranjani Mari Sundaresan
(74) *Attorney, Agent, or Firm* — Oblon, McClelland, Maier & Neustadt, L.L.P.

(57) ABSTRACT

A method transmits by a watch an information message relating to an assessment of the sleep quality of a user of the watch. The method includes the following steps: recording by the processing unit of data describing at least one event-driven episode of at least one type of environmental event recorded during a sleep period of the user; identifying at least one type of environmental event that disturbs the user's sleep by processing the descriptive data; estimating a sleep quality assessment index for the user as a function of a sleep disturbance indicator for each identified type of sleep disturbing environmental event, and devising an information message including the estimated assessment index for the purpose of diffusion to the user.

15 Claims, 1 Drawing Sheet

(58) Field of Classification Search
CPC . A61B 5/4806; A61B 5/02438; A61B 5/4809; A61B 5/4812; G04G 21/025; G04G 21/02; G16H 50/30; G04C 23/00
See application file for complete search history.

(56) References Cited

U.S. PATENT DOCUMENTS

| | | | |
|---|---|---|---|
| 10,052,061 B2* | 8/2018 | Raymann | H04W 4/70 |
| 2006/0224047 A1* | 10/2006 | Suzuki | A61B 5/1118 |
| | | | 600/595 |
| 2009/0128487 A1 | 5/2009 | Langereis et al. | |
| 2011/0190594 A1* | 8/2011 | Heit | G16H 40/67 |
| | | | 600/26 |
| 2011/0245633 A1 | 10/2011 | Goldberg et al. | |
| 2012/0173269 A1* | 7/2012 | Omidi | G16H 10/60 |
| | | | 705/2 |
| 2013/0150659 A1* | 6/2013 | Shaw | A61M 21/00 |
| | | | 600/27 |
| 2013/0278076 A1 | 10/2013 | Proud | |
| 2013/0338446 A1 | 12/2013 | Van Vugt et al. | |
| 2014/0197965 A1* | 7/2014 | Park | A61B 5/7475 |
| | | | 340/870.09 |
| 2014/0364770 A1* | 12/2014 | Slonneger | G01P 21/00 |
| | | | 600/595 |
| 2015/0164409 A1* | 6/2015 | Benson | A61B 5/1116 |
| | | | 600/595 |
| 2016/0246259 A1* | 8/2016 | Zhang | G08B 21/24 |
| 2017/0055899 A1* | 3/2017 | Bandyopadhyay | A61B 5/743 |
| 2017/0094046 A1 | 3/2017 | Raymann et al. | |
| 2018/0039232 A1* | 2/2018 | Abramov | G04G 19/12 |

FOREIGN PATENT DOCUMENTS

| | | | |
|---|---|---|---|
| JP | 2004-503283 A | | 2/2004 |
| JP | 2004290470 A | * | 10/2004 |
| JP | 2014-32572 A | | 2/2014 |
| JP | 2014-516681 A | | 7/2014 |
| WO | WO 01/95802 A1 | | 12/2001 |
| WO | WO 2007/107900 A2 | | 9/2007 |
| WO | WO 2011/109716 A2 | | 9/2011 |
| WO | WO 2012/156427 A1 | | 11/2012 |

OTHER PUBLICATIONS

European Search Report issued Mar. 28, 2019 in European Application 18202782.1 filed on Oct. 26, 2018 (with English Translation of Categories of Documents & Written Opinion).
Korean Office Action issued Jan. 10, 2021 in Korean Patent Application No. 10-2019-0134129 (with English translation).
Chinese Office Action issued Dec. 28, 2022 in Chinese Application No. 201911037794.8 with English translation, 14 pgs.
Combined Chinese Office Action And Search Report issued Sep. 14, 2023 in Chinese Patent Application No. 201911037794.8 (with English Translation of Office Action only), 15 pages.

* cited by examiner

METHOD OF TRANSMISSION BY A WATCH OF AN INFORMATION MESSAGE RELATING TO AN ASSESSMENT OF THE SLEEP QUALITY OF A USER OF SAID WATCH

CROSS-REFERENCE TO RELATED APPLICATION

This application claims priority to European Patent Application No. 18202782.1 filed on Oct. 26, 2018, the entire disclosure of which is hereby incorporated herein by reference.

FIELD OF THE INVENTION

The present invention concerns a method of transmission by a watch of an information message relating to an assessment of the sleep quality of a user of said watch and a system implementing such a method.

The invention also concerns a watch comprising such a system together with a computer programme.

PRIOR ART

Sleep is a state in which a person's body restores itself, for example defending itself against infection or producing hormones. The quality of this sleep directly affects our mental, moral and physical health. In such a context, it is thus understood that it is important to be able to assess the quality of a person's sleep in order, particularly, to improve it if necessary.

To achieve this, methods are known in the state of the art which provide for assessment of a person's sleep quality by implementing processing of measurement data generally obtained from motion sensors or physiological sensors.

However, one of the major drawbacks of such methods lies in the fact that the sleep quality assessment offered is often imprecise or erroneous, because it is produced from measurement data, which is sometimes difficult to obtain, and which is not always directly related to conditions relating to sleep quality.

It is understood that there is a need to find an alternative solution, particularly one which does not have the drawbacks of the prior art.

SUMMARY OF THE INVENTION

It is therefore an object of the present invention to offer a method of transmission by a watch of an information message relating to a sleep quality assessment which is reliable and simple to implement.

To this end, the invention concerns a method of transmission by a watch of an information message relating to an assessment of the sleep quality of a user of said watch, the method including the following steps:
  recording by the processing unit of data describing at least one event-driven? episode of at least one type of environmental event recorded during a sleep period of the user;
  identifying at least one type of environmental event that disturbs the user's sleep by processing said descriptive data;
  estimating a sleep quality assessment index for the user as a function of a sleep disturbance indicator for each identified type of environmental event that disturbs sleep, and
  devising an information message including the estimated assessment index for the purpose of transmission to the user.

In other embodiments:
  the identification step includes a sub-step of selecting one or more event-driven episodes relating to each type of environmental event recorded during the user's sleep period using at least one selection criterion;
  a first selection criterion provides that at least one environmental measurement of the descriptive data of each event-driven episode relating to each type of environmental event is compared to a reference threshold of sleep disturbance;
  a second selection criterion consists in comparing a duration of each event-driven episode relating to each type of environmental event to a reference threshold of duration of sleep disturbance;
  the identification step includes a sub-step of generating a sleep disturbance indicator for each identified type of environmental event that disturbs sleep;
  the generation sub-step includes a phase of calculating the sleep disturbance indicator for each identified type of sleep disturbing environmental event using the following descriptive characteristics:
    a mean value of the environmental measurement(s) comprised in the descriptive data of the selected event-driven episodes relating to this type of environmental event;
    a total duration of this type of environmental event;
    the number of selected event-driven episodes of this type of environmental event;
    the start and end times of the selected event-driven episodes of this type of environmental event.

The invention also concerns a system of transmission by a watch of an information message relating to an assessment of the sleep quality of a user of said watch that implements such a method, the system comprising the following elements which are connected to each other: a processing unit, at least one environmental sensor and an interface for diffusing visual and/or audio information.

The invention also concerns a watch comprising such a system.

Advantageously, the watch is a connected mechanical watch.

The invention also concerns a computer programme comprising programme code instructions for execution of the steps of this method when said programme is executed by a processing unit.

BRIEF DESCRIPTION OF THE DRAWINGS

Other features and advantages will appear clearly from the following description, given by way of non-limiting illustration, with reference to the annexed Figures, in which.

DETAILED DESCRIPTION OF THE INVENTION

Figure 1:
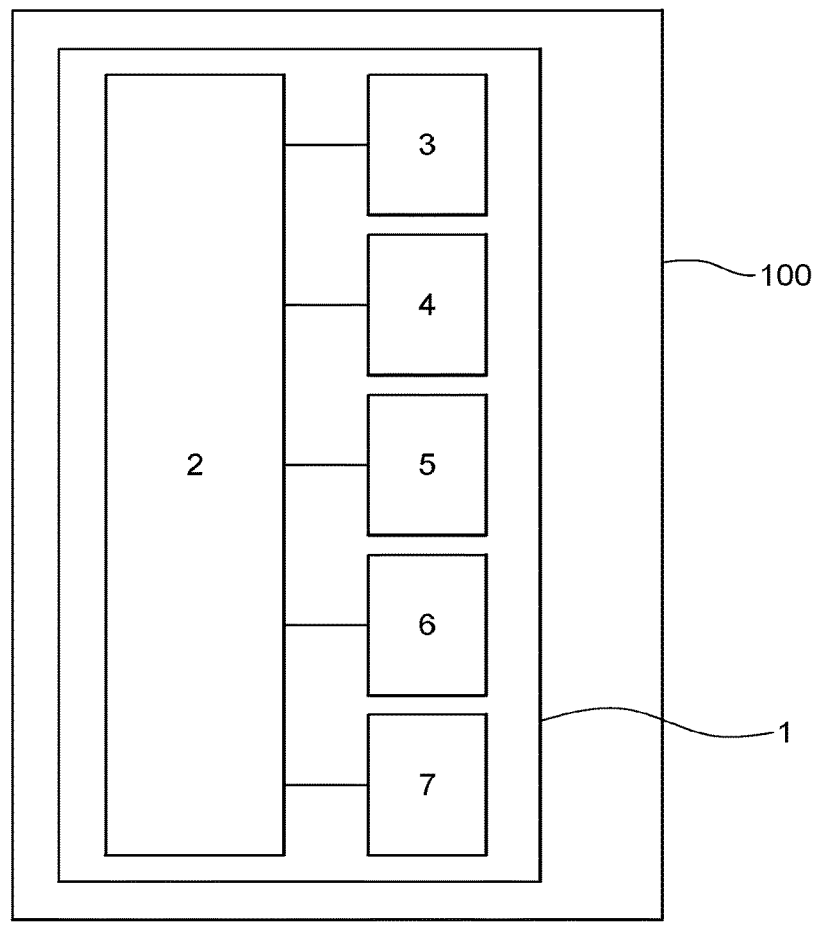
FIG. 1 is a schematic representation of a watch comprising a system for transmitting an information message relating to an assessment of the sleep quality of the user of said watch, according to one embodiment of the invention.

FIG. 1 represents a watch 100 comprising the system 1 for transmitting by watch 100 of an information message relating to an assessment of the sleep quality of a user of said watch 100. This system 1 is contained in watch 100 which is preferably a connected mechanical watch 100 with a hybrid display. System 1 more specifically includes, in a non-limiting and/or non-exhaustive manner:

- a processing unit 2 including material and software resources, in particular, at least one processor cooperating with memory elements;
- an interface for transmitting visual information 3, such as a hybrid display dial provided with a first analogue display component and a second digital and/or alphanumeric display component;
- an interface for transmitting audio information 4 such as a loudspeaker;
- a communication interface;
- at least one environmental sensor 5;
- at least one behavioural sensor 6, and
- at least one physiological sensor 7.

In this system 1, processing unit 2 is connected, amongst other things, to the visual and audio information transmission interfaces and to the environmental, behavioural and physiological sensors 5, 6, 7.

System 1 in this watch 100 is capable of assessing the sleep quality of the user preferably simply from at least one type of environmental event recorded during a sleep period of the user. Each type of recorded event is quantified using at least one event-driven episode which is specific thereto and which occurs during the user's sleep period. Each event-driven episode is characterized by descriptive data including, in particular, one or more measurements of an environmental parameter. This environmental parameter is a quantity relating to a characteristic of the environment in which watch 100 and its user are located. Such a parameter relates, in a non-limiting and/or non-exhaustive manner to: a temperature, relative humidity, ambient noise level, atmospheric pressure, illumination, movement, air quality, etc. . . .

By way of example, when the parameter corresponds to a 'noise level', an event-driven episode is defined by the following descriptive data:

- one or more measurements of this noise level are determined by at least one suitable environmental sensor 5 and transmitted to processing unit 2;
- the duration of the event-driven episode which is calculated by processing unit 2 is, for example, 10 minutes, and
- the start time 10 am and the end time 10:10 are determined by processing unit 2.

It is understood that, at this stage, this environmental event relates to a 'noise level', and that for this type of event several episodes with different descriptive data can then be estimated during the sleep period. Subsequently, according to the method described below, if this type of environmental event is considered to disturb the user's sleep, it then becomes a 'noise nuisance'.

In this context, environmental sensors 5 are specifically adapted to measure these environmental parameters. As will be seen below, the other behavioural and physiological sensors 6 and 7 participate in the making of measurements which may optionally be used by processing unit 2 in order to assess the user's sleep quality. Behavioural sensors 6 are capable of measuring all types of behavioural characteristics of the user of watch 100, such as for example, movements or gestures made by the user during the sleep period. To this end, these behavioural sensors 6 may comprise one or more inertial sensors, of the miniature multi-axis accelerometer, gyroscope or rate gyro type, such as multi-axis sensors made in MEMS technology, capable of detecting angular speeds and linear accelerations along several axes combining accelerometers and/or gyroscopes. As regards physiological sensors 7, these are capable of measuring parameters relating to the working of a user's organism, such as, for example, the pulse, blood oxygen saturation, skin impedance, respiratory rate, respiratory arrhythmia, skin temperature, sweat rate, blood oxygen saturation or blood flow.

Figure 2:
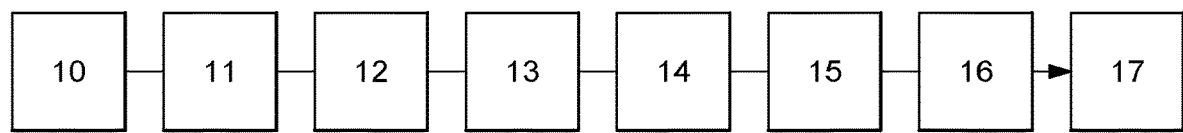
FIG. 2 is a logic diagram relating to a method for transmitting this information message according to the embodiment of the invention.

This system 1 of watch 100 is capable of implementing a method for transmission by watch 100 of this information message represented in FIG. 2.

This method includes a step 10 of recording, by processing unit 2, data describing at least one event-driven episode of at least one type of environmental event recorded during a sleep period of the user. During this step 10, from detection of the start of the user's sleep period until the end of this period, the descriptive data of one or more event-driven episodes of at least one type of environmental event are archived in the memory elements of processing unit 2 of watch 100. This descriptive data of each event-driven episode includes, in a non-exhaustive and non-limiting manner:

- one or more environmental measurements determined by the corresponding sensors 5 and transmitted to processing unit 2:
- the duration of the event-driven episode, which is calculated by processing unit 2, and
- the start and end times of the episode which are determined by processing unit 2.

It will be noted that the creation of an episode is linked to identification by processing unit 2 of a variation in an environmental parameter relating to a corresponding type of environmental event.

In this context, the start of the sleep period can be determined from an illuminance measurement by an environmental sensor 5 such as an illumination meter. Thus, the start time of the sleep period can be identified as soon as a low lighting condition is determined by processing unit 2, for example when the illuminance measurement transmitted by sensor 5 is below a reference threshold of light intensity for a determined period of time. Alternatively, the start of the sleep period can be detected from physiological measurement data and/or behavioural measurement data about the user. For example, processing unit 2 can determine the start time of this sleep period when behavioural sensor 6, for example the inertial sensor, indicates that the user is immobile for a determined length of time. In a variant, processing unit 2 can use additional information such as the time of day and an estimation of the user's circadian rhythm. For example, the sleep start time can only be detected during a specific time of day, when the user is expected to fall asleep. Similarly, the end of the sleep period can be determined from an illuminance measurement, as soon as a strong lighting condition is thus determined by processing unit 2, for example when the illuminance measurement transmitted by sensor 5 is greater than the reference threshold of light intensity for a determined period of time. Alternatively, processing unit 2 can estimate the end of the sleep period, for example, when the behavioural measurement data relating to the user's potential motion indicates that he has got up.

The method then includes a step 11 of identifying at least one type of environmental event disturbing the user's sleep by processing said descriptive data. To this end, this step 11 includes a sub-step 12 of selecting one or more event-driven episodes relating to each type of environmental event recorded during the user's sleep period using at least one selection criterion. According to a first selection criterion, at least one environmental measurement of the descriptive data of each event-driven episode relating to each type of environmental event is compared to a reference threshold of sleep disturbance. If said at least one measurement is greater than the reference threshold of sleep disturbance, then the episode can be selected or preselected when the conditions of selection are linked to verification of a second selection criterion. This second selection criterion consists in comparing the duration of each event-driven episode relating to each type of environmental event to a reference threshold of duration of sleep disturbance. In this context, if the duration of the episode is greater than the reference threshold of duration of sleep disturbance, then the episode is selected.

Identification step 11 then includes a sub-step 13 of detecting one or more types of environmental events disturbing the sleep of the user of watch 100, from the event-driven episodes that were selected. This sub-step can provide that, for a given type of environmental event, the number of episodes of this event must be higher than a reference threshold in order to be detected.

Subsequently, identification step 11 includes a sub-step 14 of generating a sleep disturbance indicator for each identified/detected type of sleep disturbing environmental event. This sub-step 14 includes a phase 15 of calculating the sleep disturbance indicator for each identified type of sleep disturbing environmental event from descriptive characteristics. These descriptive characteristics of each identified type of sleep disturbing environmental event are as follows:

- a mean value of the environmental measurement(s) comprised in the descriptive data of the selected event-driven episodes;
- the total duration of this type of sleep disturbing environmental event during the sleep period of the user of watch 100 which is equal to the sum of the durations of the selected event-driven episodes;
- the number of selected event-driven episodes;
- the start and end times of the selected event-driven episodes which make it possible to assess their effect/impact on the disturbance of sleep cycles. Indeed, the user's sleep period includes a series of cycles with NREM sleep phases, especially early in the night, which allow the body to recover physically, and of REM sleep which corresponds to the time when the user dreams or releases nervous tension.

It will be noted that calculation of the sleep disturbance indicator is performed according to one or more of these descriptive characteristics.

Further, this identification step 11 can be implemented as soon as the sleep period ends or simultaneously with recording step 10, i.e. at the start of the sleep period.

The method then includes a step 16 of estimating a sleep quality assessment index as a function of the sleep disturbance indicator for each identified type of sleep disturbing environmental event. In this step 16, processing unit 2 determines the sleep quality assessment index by calculating a mean value of the sleep disturbance indicator(s) obtained in generation sub-step 14. During this calculation, coefficients can be applied to some indicators according to the nature of the type of sleep disturbing environmental event to which they relate. Indeed, certain types of events may have a greater impact on sleep disturbance than others.

It will be noted that, optionally, physiological and/or behavioural measurement data produced during the event-driven episodes can also be taken into account in calculating this index.

Next, the method includes a step 17 of devising the information message including the estimated assessment index for the purpose of diffusion to the user. Such an information message may be an audio message or a visual message comprising a two-dimensional or three-dimensional graphic representation including the index. In addition to the sleep quality assessment index, this message may include a recommendation for the user of watch 100 relating to an attitude (or behaviour) to adopt in order to improve sleep quality, which is defined as a function of the value of this index and thus of the assessed sleep quality level.

It will be noted that the method can also provide a step during which the user can share his sleep assessment by selecting, in a pop-up menu displayed in a second display component of the dial, a criterion for rating sleep from a list of criteria including, for example, the following elements a good night/sleep, a restful night/sleep, a difficult night/sleep, etc. . . .

This step then provides for the archiving of this assessment by the watch user in the form of data which, when processed by the processing unit, can improve the precision of sleep assessment by the present method and system.

The invention also concerns a computer programme including programme code instructions for the execution of steps 10 to 17 of this method when said programme is executed by processing unit 2 of watch 100.

The invention claimed is:

1. A method of transmission by a watch of an information message relating to an assessment of sleep quality of a user of said watch, the method comprising:
  - determining whether a sleep period of the user has started based on whether light intensity measured by a sensor of the watch is below a threshold value for a predetermined period of time and whether an ambient noise level measured by a sensor of the watch is below a threshold value for a predetermined period of time, the determining being performed during a specific time of day when the user is expected to fall asleep, without being performed during another time of the day when the user is not expected to fall asleep;
  - in response to determining that the sleep period of the user has started, recording, by processing circuitry of the watch, data describing at least one event-driven episode of at least one type of environmental event recorded during the sleep period of the user;
  - identifying, by the processing circuitry of the watch, at least one type of environmental event that disturbs the user's sleep by processing said descriptive data;
  - receiving, via an interface of the watch, the interface including a hybrid display dial, which includes an analog display and a digital display, an input from the user of a self-sleep assessment indicating the user's own assessment of the user's sleep, the self-sleep assessment including a good night sleep, a restful night sleep, or a difficult night sleep, the input being provided via the digital display of the hybrid display dial of the watch;
  - estimating, by the processing circuitry of the watch, a sleep quality assessment index for the user as a function of a sleep disturbance indicator for each identified type of sleep disturbing environmental event and the self-sleep assessment indicating the user's own assessment of the user's sleep, the self-sleep assessment including the good night sleep, the restful night sleep, or the difficult night sleep; and
  - generating, by the processing circuitry of the watch, a two-dimensional or three-dimensional graphic representation of the information message including the estimated assessment index for diffusion to the user.

2. The method according to claim 1, wherein the identifying comprises selecting one or more event-driven episodes relating to each type of environmental event recorded during the sleep period of the user using at least one selection criterion.

3. The method according to claim 2, wherein a first selection criterion of the at least one selection criterion provides that at least one environmental measurement of the descriptive data of each event-driven episode relating to each type of environmental event is compared to a reference threshold of sleep disturbance.

4. The method according to claim 3, wherein a second selection criterion of the at least one selection criterion comprises comparing a duration of each event-driven episode relating to each type of environmental event to a reference threshold of duration of sleep disturbance.

5. The method according to claim 1, wherein the identifying comprises generating a sleep disturbance indicator for each identified type of sleep disturbing environmental event.

6. The method according to claim 5, wherein the generating comprises a phase of calculating the sleep disturbance indicator for each identified type of sleep disturbing environmental event using the following descriptive features:
 a mean value of environmental measurement(s) comprised in the descriptive data of the selected event-driven episodes relating to the type of sleep disturbing environmental event;
 a total duration of the type of sleep disturbing of environmental event;
 the number of selected event-driven episodes of the type of sleep disturbing environmental event; and
 the start and end times of the selected event-driven episodes of the type of sleep disturbing environmental event.

7. The method according to claim 1, wherein
 the input from the user of the self-sleep assessment is provided via a selection from a list displayed in a pop-up menu on the digital display of the hybrid display dial of the watch.

8. The method according to claim 7, wherein
 the list displayed in the pop-up menu on the digital display of the hybrid display dial of the watch includes the good night sleep, the restful night sleep, and the difficult night sleep.

9. The method according to claim 1, wherein
 the identifying comprises selecting one or more event-driven episodes relating to each type of environmental event recorded during the sleep period of the user using at least one selection criterion,
 a first selection criterion of the at least one selection criterion provides that at least one environmental measurement of the descriptive data of each event-driven episode relating to each type of environmental event is compared to a reference threshold of sleep disturbance, and
 a second selection criterion of the at least one selection criterion comprises comparing a duration of each event-driven episode relating to each type of environmental event to a reference threshold of duration of sleep disturbance.

10. The method according to claim 1, wherein the information message includes a recommendation for the user of the watch relating to an attitude or behavior to adopt to improve sleep quality.

11. A system of transmission by a watch of an information message relating to an assessment of sleep quality of a user of said watch, the system comprising:
 at least one environmental sensor;
 an interface to diffuse visual and/or audio information, the interface including a hybrid display dial, which includes an analog display and a digital display; and
 processing circuitry configured to
  determine whether a sleep period of the user has started based on whether light intensity measured by a sensor of the watch is below a threshold value for a predetermined period of time and whether an ambient noise level measured by a sensor of the watch is below a threshold value for a predetermined period of time, the determination being performed during a specific time of day when the user is expected to fall asleep, without being performed during another time of the day when the user is not expected to fall asleep,
  in response to determining that the sleep period of the user has started, record data describing at least one event-driven episode of at least one type of environmental event, from the at least one environment sensor, recorded during the sleep period of the user,
  identify at least one type of environmental event that disturbs the user's sleep by processing said descriptive data,
  receive, via the interface, an input from the user of a self-sleep assessment indicating the user's own assessment of the user's sleep, the self-sleep assessment including a good night sleep, a restful night sleep, or a difficult night sleep, the input being provided via the digital display of the hybrid display dial,
  estimate a sleep quality assessment index for the user as a function of a sleep disturbance indicator for each identified type of sleep disturbing environmental event and the self-sleep assessment indicating the user's own assessment of the user's sleep, the self-sleep assessment including the good night sleep, the restful night sleep, or the difficult night sleep, and
  generate a two-dimensional or three-dimensional graphic representation of the information message including the estimated assessment index for diffusion, via the interface, to the user.

12. A watch comprising the system according to claim 11.

13. The watch according to claim 12, wherein the watch is a connected mechanical watch.

14. The system according to claim 11, wherein
 the processing circuitry is configured to identify the at least one type of environmental event by generating a sleep disturbance indicator for each identified type of sleep disturbing environmental event, the generating comprising a phase of calculating the sleep disturbance indicator for each identified type of sleep disturbing environmental event using the following descriptive features:
 a mean value of environmental measurements, which include humidity and atmospheric pressure measurements, comprised in the descriptive data of the selected event-driven episodes relating to the type of sleep disturbing environmental event;
 a total duration of the type of sleep disturbing of environmental event;
 the number of selected event-driven episodes of the type of sleep disturbing environmental event; and
 the start and end times of the selected event-driven episodes of the type of sleep disturbing environmental event.

15. A non-transitory computer-readable storage medium including computer executable instructions, wherein the instructions, when executed by a computer, cause the computer to perform a method of transmission by a watch of an information message relating to an assessment of sleep quality of a user of said watch, the method comprising:

determining whether a sleep period of the user has started based on whether light intensity measured by a sensor of the watch is below a threshold value for a predetermined period of time and whether an ambient noise level measured by a sensor of the watch is below a threshold value for a predetermined period of time, the determining being performed during a specific time of day when the user is expected to fall asleep, without being performed during another time of the day when the user is not expected to fall asleep;

in response to determining that the sleep period of the user has started, recording data describing at least one event-driven episode of at least one type of environmental event recorded during the sleep period of the user;

identifying at least one type of environmental event that disturbs the user's sleep by processing said descriptive data;

receiving, via an interface of the watch, the interface including a hybrid display dial, which includes an analog display and a digital display, an input from the user of a self-sleep assessment indicating the user's own assessment of the user's sleep, the self-sleep assessment including a good night sleep, a restful night sleep, or a difficult night sleep, the input being provided via the digital display of the hybrid display dial of the watch;

estimating a sleep quality assessment index for the user as a function of a sleep disturbance indicator for each identified type of sleep disturbing environmental event and the self-sleep assessment indicating the user's own assessment of the user's sleep, the self-sleep assessment including the good night sleep, the restful night sleep, or the difficult night sleep; and generating a two-dimensional or three-dimensional graphic representation of the information message including the estimated assessment index for diffusion to the user.

* * * * *